United States Patent
Sawchuk et al.

(10) Patent No.: US 12,215,991 B2
(45) Date of Patent: Feb. 4, 2025

(54) PROVERLESS LIQUID HYDROCARBON FLOW MEASUREMENT FOR PIPELINE

(71) Applicant: Canada Pipeline Accessories Company, Ltd., Calgary (CA)

(72) Inventors: Blaine Sawchuk, De Winton (CA); Dale Sawchuk, Calgary (CA); Daniel Sawchuk, Chestermere (CA)

(73) Assignee: Canada Pipeline Accessories Company, Ltd., Calgary (CA)

( * ) Notice: Subject to any disclaimer, the term of this patent is extended or adjusted under 35 U.S.C. 154(b) by 179 days.

(21) Appl. No.: 17/983,435

(22) Filed: Nov. 9, 2022

(65) Prior Publication Data
US 2023/0160733 A1 May 25, 2023

Related U.S. Application Data

(60) Provisional application No. 63/281,174, filed on Nov. 19, 2021.

(51) Int. Cl.
| | | |
|---|---|---|
| *G01F 1/74* | (2006.01) | |
| *G01F 1/36* | (2006.01) | |
| *G01N 33/28* | (2006.01) | |

(52) U.S. Cl.
CPC .............. *G01F 1/74* (2013.01); *G01F 1/366* (2013.01); *G01N 33/28* (2013.01)

(58) Field of Classification Search
CPC ............ G01F 1/74; G01F 1/366; G01N 33/28
See application file for complete search history.

(56) References Cited

U.S. PATENT DOCUMENTS

| | | | |
|---|---|---|---|
| 3,457,768 A | | 7/1969 | Jasek |
| 5,063,776 A | * | 11/1991 | Zanker .................... G01F 1/002 73/152.21 |

(Continued)

FOREIGN PATENT DOCUMENTS

| | | |
|---|---|---|
| CN | 104316115 A | 1/2015 |
| WO | 2023212826 A1 | 9/2023 |

OTHER PUBLICATIONS

Sawchuk, B., Effects of Flow Conditioning for Liquid Measurement, 89th International School of Hydrocarbon Measurement, Class #2120.1, p. 1-28, 2014.

(Continued)

*Primary Examiner* — Kristina M Deherrera
*Assistant Examiner* — Jean F Morello
(74) *Attorney, Agent, or Firm* — CAHN & SAMUELS, LLP

(57) ABSTRACT

A system for operating a flow meter in a pipeline includes at least one flow conditioner or mixer installed in a pipeline; at least one volumetric flow meter installed downstream from the at least one flow conditioner or mixer for measuring velocity of a fluid in the pipeline; a pair pressure transmitters for measuring fluid pressure at a first side and a second side of the at least one flow conditioner or mixer; and a flow computer, connected to the pair of pressure transmitters and to the at least one flow meter. The flow computer includes 1) at least one database having experimental Reynolds number data for the at least one flow meter for a plurality of fluids, and 2) a processor having programmable logic for calculating viscosity of a fluid in the pipeline and operating the flow meter when the fluid in the pipeline changes.

14 Claims, 3 Drawing Sheets

(56) References Cited

U.S. PATENT DOCUMENTS

| | | | |
|---|---|---|---|
| 6,332,111 | B1 | 12/2001 | Fincke |
| 6,463,810 | B1 | 10/2002 | Liu |
| 7,328,113 | B2 | 2/2008 | Rothman et al. |
| 7,607,361 | B2 | 10/2009 | Unalmis et al. |
| 8,136,414 | B2 | 3/2012 | Steven |
| 8,448,525 | B2 | 5/2013 | Wehrs et al. |
| 8,820,178 | B2 | 9/2014 | Ayers et al. |
| 9,605,987 | B2 * | 3/2017 | Wee .......................... G01F 1/50 |
| 2010/0191481 | A1 | 7/2010 | Steven |
| 2010/0224009 | A1 | 9/2010 | Steven |
| 2014/0013857 | A1 | 1/2014 | Lupeau et al. |
| 2016/0084687 | A1 | 3/2016 | Steven |
| 2016/0187172 | A1 | 6/2016 | Gottlieb |
| 2016/0238423 | A1 | 8/2016 | Steven et al. |
| 2016/0245684 | A1 * | 8/2016 | Wee .......................... G01F 1/50 |
| 2016/0303527 | A1 | 10/2016 | Hodges |

OTHER PUBLICATIONS

Rabone, J., Prognosis Applied to High Viscosity Flows, South East Asia Flow Measurement Conference, p. 1-31, Mar. 4-5, 2014.

Marshall, C., A Differential Pressure Meter for Low Reynolds No. Application, 35th International North Sea Flow Measurement Workshop, p. 1-27, Oct. 24-26, 2017.

Marshall, C., Advances in Flow Measurement Using a Frictional Pressure Drop, North Sea Flow Measurement Workshop, p. 1-24, Oct. 22-24, 2018.

Sawchuk, B., Flow Conditioning for Fluid Flow Measurement, 94th International School of Hydrocarbon Measurement, Class #1330.1, p. 1-19, 2019.

Morrison et al., "Euler Number Based Orifice Discharge Coefficient Relationship", J. Fluids Eng 125(1), 189-191 (2003).

Espacenet, English abstract for CN104316115A, Jan. 28, 2015.

English Abstract of CN104316115A, Jan. 28, 2015.

* cited by examiner

PROVERLESS LIQUID HYDROCARBON FLOW MEASUREMENT FOR PIPELINE

This patent application claims priority to U.S. Ser. No. 63/281,174 filed on Nov. 19, 2021 in the U.S. Patent and Trademark Office, the entirety of which is incorporated by reference.

FIELD OF INVENTION

The present invention is directed to a system and methods for operating a flow meter in a fluid pipeline, in particular operating a flow meter in an oil, crude oil, or liquified natural gas (LNG) pipeline based upon Reynolds number, without the need for a meter proving device or a viscometer or a densitometer. The system and methods may be used for any liquid flow or a liquid flow of a single phase multicomponent fluid. The present invention applies to volumetric flow meters, for example, turbine flow meters or ultrasonic flow meters.

BACKGROUND OF THE INVENTION

It is known to collect and process information from flow meters and/or ancillary equipment in a pipeline. Normally, an expensive meter proving device is installed. The meter proving device is used to calibrate a flow meter in a meter run against actual volumetric flow rate. If the fluid type in the pipeline is changed (thereby impacting the density and/or viscosity of the fluid and/or the speed of sound), a new meter proof must be carried out at exorbitant cost. This is done numerous times, sometimes several times per shift.

Normally viscosity is not measured. Density may not be measured either. The flow meter is run against actual volumetric flow rate, which is dependent on density, viscosity, temperature, composition and pressure (i.e., Reynolds number).

It is an advantage of the present invention that a flow meter in a fluid pipeline may be operated without at least one of a meter proving device, densitometer, viscometer, or any combination thereof.

SUMMARY OF INVENTION

The invention provides a method for operating a flow meter in a pipeline including measuring a pressure of the fluid on a first and a second side of at least one flow conditioner or mixer; measuring velocity of a fluid in a pipeline with a flow meter downstream of the at least one flow conditioner or mixer; with an initial estimate of the fluid density, calculating a k factor from the Euler equation; obtaining a first Reynolds number from the calculated k factor and from experimental Reynolds number data for the flow meter for a plurality of fluids; calculating a coefficient of discharge Cd for the fluid; and obtaining a second Reynolds number from the calculated Cd and from experimental Reynolds number data for the flow meter for a plurality of fluids.

The invention provides in at least one method embodiment further to any of the previous embodiments a method that may be reiterated until the first Reynolds number and the second Reynolds number are a substantially similar third Reynolds number.

The invention provides in at least one method embodiment further to any of the previous embodiments a method that further includes calculating a viscosity of the fluid from the third substantially similar Reynolds number.

The invention provides in at least one method embodiment further to any of the previous embodiments a method that further includes providing density and viscosity measurements directly to a flow meter when a fluid in the pipeline changes.

The invention provides a system for operating a flow meter in a pipeline including at least one flow conditioner or mixer installed in a pipeline; at least one flow meter installed downstream from the at least one flow conditioner or mixer for measuring velocity of a fluid in the pipeline; and a pair of pressure transmitters for measuring fluid pressure at a first side and a second side of the at least one flow conditioner or mixer. A flow computer is connected to the pair of pressure transmitters and to the at least one flow meter. The flow computer includes 1) at least one database having experimental Reynolds number data for the at least one flow meter for a plurality of fluids, and 2) a processor having programmable logic for calculating viscosity of a fluid in the pipeline and operating the flow meter when the fluid in the pipeline changes.

The invention provides in at least one system embodiment further to any of the previous embodiments a flow meter that is an ultrasonic meter.

The invention provides in at least one system embodiment further to any of the previous embodiments a flow meter that is a turbine meter.

The invention provides in at least one system embodiment further to any of the previous embodiments a system that does not have a flow meter proving device.

The invention provides in at least one system embodiment further to any of the previous embodiments a system that does not have a viscometer.

Given the following enabling description of the drawings, the methods and systems should become evident to a person of ordinary skill in the art.

In the detailed description, references to "one embodiment", "an embodiment", or "in embodiments" mean that the feature being referred to is included in at least one embodiment of the invention. Moreover, separate references to "one embodiment", "an embodiment", or "in embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

DETAILED DESCRIPTION OF THE INVENTION

The present invention is directed to a system and methods for operating a flow meter in a fluid pipeline, in particular, operating a flow meter in an oil, crude oil, or liquified natural gas (LNG) pipeline using Reynolds number, without the need for a meter proving device or a viscometer when the fluid in the pipeline changes.

According to the present invention, a flow or volumetric meter may be used in a pipeline. The flow or volumetric meter is calibrated once against Reynolds number, for example at a remote calibration facility, for a plurality of fluids. As discussed below, if the density and/or viscosity of a fluid in the pipeline is changed, the flow or volumetric meter can be operated against Reynolds number, thus allowing for a single flow meter curve to be used for many different fluid types at different times.

The system and methods of the present invention provide viscosity and density, thereby allowing a flow or volumetric meter to be operated against Reynolds number. Thus, the flow or volumetric meter can provide accurate flow measurement when the fluid characteristics change, thereby eliminating the need for procurement and installation of at least one of costly meter proving devices, densitometers, or viscometers.

According to an embodiment of the present invention, a flow or volumetric meter may be a turbine meter or an ultrasonic meter.

Figure 1:
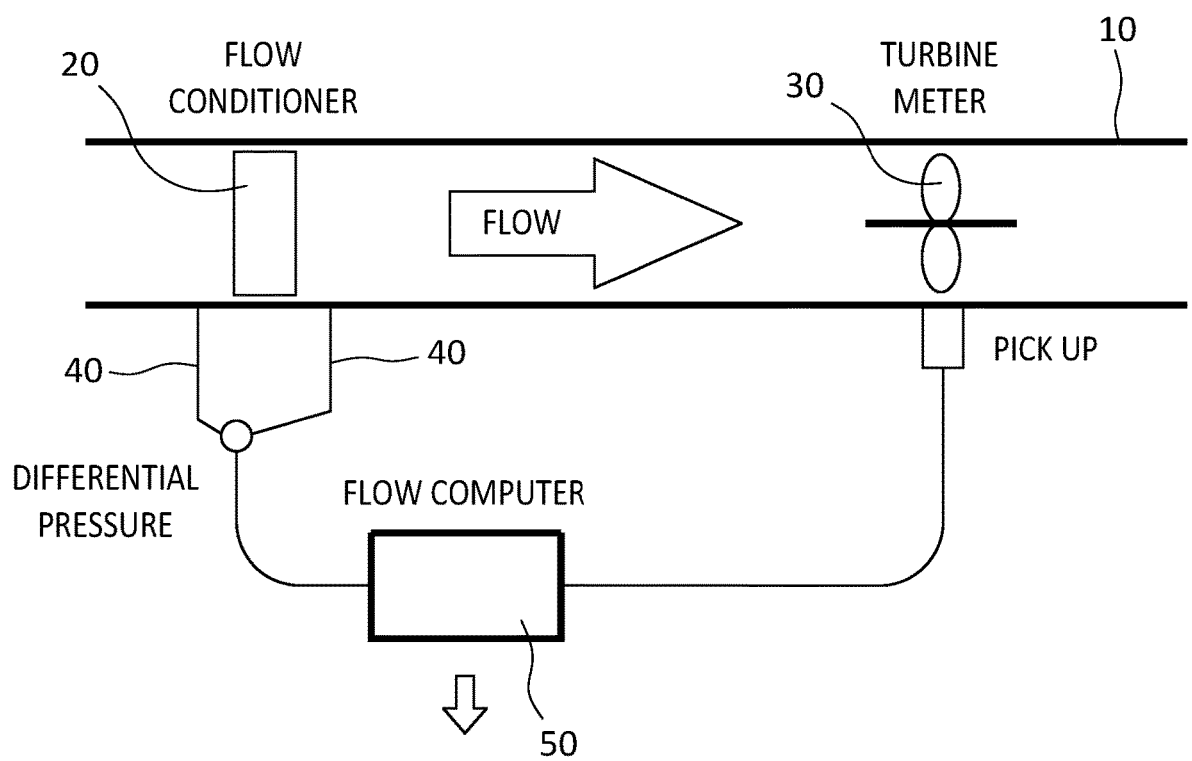
FIG. 1 is a schematic of a system according to an embodiment of the present invention.

FIG. 1 is a schematic of a system according to an embodiment of the present invention. A fluid flow pipeline 10 has at least one flow conditioner or mixer 20 and a downstream flow or volumetric meter 30 (e.g., an ultrasonic or turbine meter). A pair of pressure transmitters 40 measure the pressure on a first and a second side of the at least one flow conditioner or mixer 20. A flow computer 50 receives pressure measurements from the pair of pressure transmitters 40 and velocity measurements from the flow meter 30 and adjusts the flow meter automatically as follows. The flow computer may be connected (e.g., via direct electrical wires or wirelessly) to the pair of pressure transmitters and to the flow meter.

Beginning with the Euler Equation, a k factor is calculated by measuring the pressure differential from the pair of pressure transmitters; measuring the velocity from the flow or volumetric meter; and estimating or guessing a density value of the fluid in the pipeline. At the same time, the flow coefficient φ is obtained from a database of fluid dynamics behavior, which database may contain experimental data obtained by collecting differential pressures from the flow conditioner and fluid properties from a pipeline:

$$\Delta P = \tfrac{1}{2}\rho k\varphi V^2 \tag{1}$$

Figure 2:
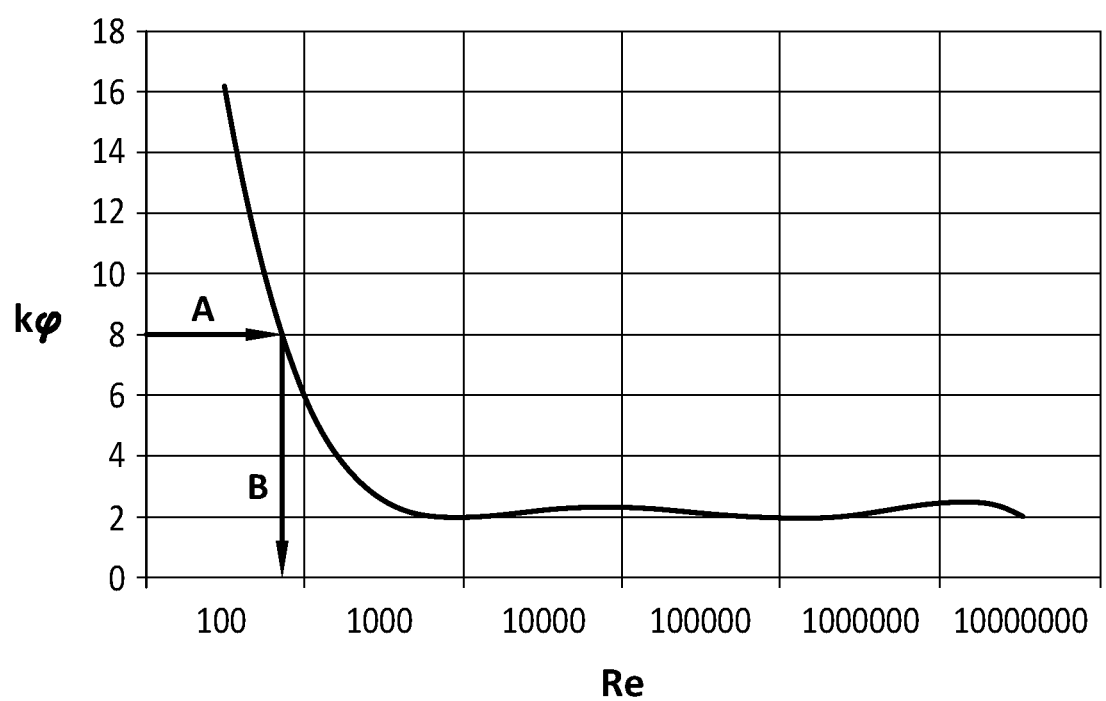
FIG. 2 shows a graph of experimental data of k factor vs. Reynolds number for a flow meter for a plurality of fluids.

Using the calculated kφ factor, a first Reynolds number (Re) for the fluid is determined from experimental data, for example from FIG. 2. FIG. 2 is exemplary graph of kφ factor versus Reynolds number for the flow meter that was previously calibrated for a plurality of fluids. In embodiments, the experimental data may be stored in the flow computer or a distributed control system.

With the first obtained Re number, the initial estimated density value, and measured differential pressure and velocity, the Coefficient of Discharge (Cd) for the at least one flow conditioner or mixer is calculated from the following orifice flow meter equation:

$$V_{meter} = C_d E_v \frac{\pi}{4} d^2 \sqrt{\frac{2\Delta P}{\rho}} \tag{2}$$

Figure 3:
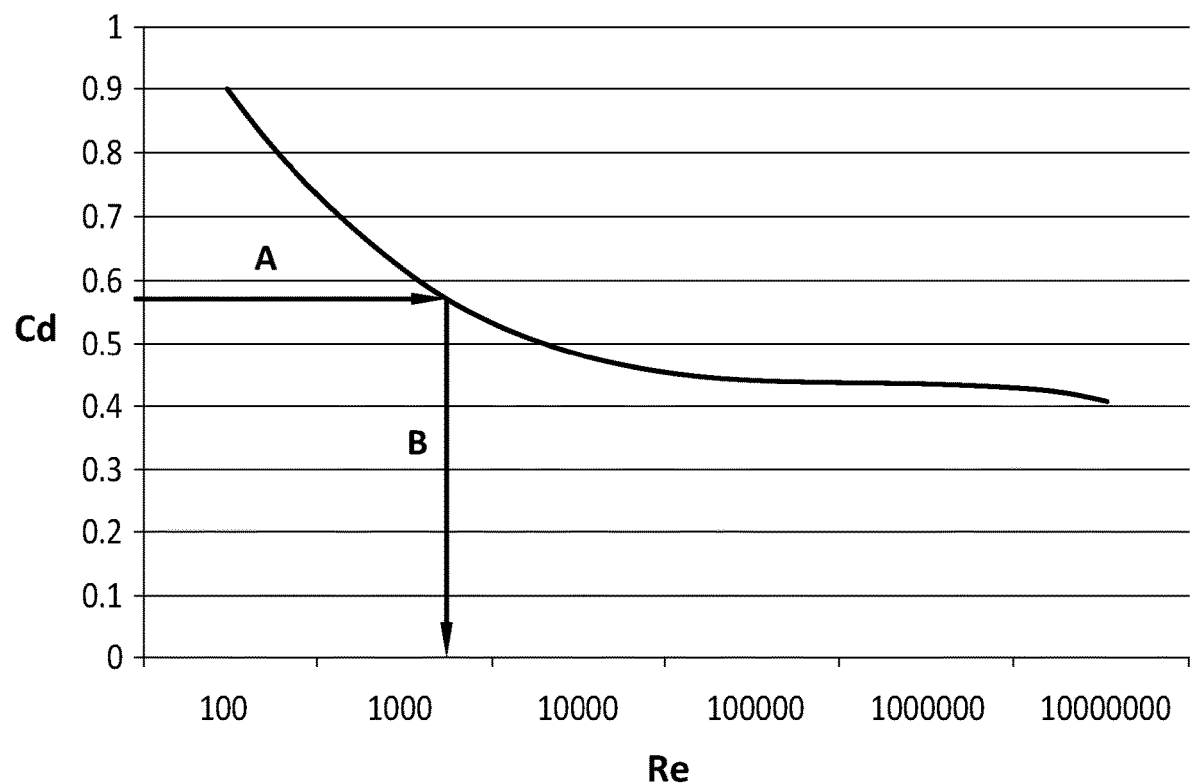
FIG. 3 shows a graph of experimental data of Cd vs. Reynolds number for a flow meter for a plurality of fluids.

Using the calculated Cd factor, a second Reynolds number (Re) for the fluid is determined from FIG. 3. FIG. 3 is exemplary graph of Cd versus Reynolds number for the flow or volumetric meter that was previously calibrated for a plurality of fluids. In embodiments, the calibration data may be stored in the flow computer or a distributed control system.

With this second obtained Reynolds number, another density estimate is made for the fluid and the process is repeated until the first Reynolds number (obtained via the kφ factor from FIG. 1) and the second Reynolds number (obtained from Cd via FIG. 3) produce a substantially same third Reynolds number.

With this third substantially same Reynolds number, and with the measured fluid velocity from the volumetric meter, pipe diameter, and the final density estimate, the viscosity of the fluid may be calculated from the following Reynolds number equations:

$$Re = \frac{\rho L \overline{U}}{\mu} \tag{3}$$

or $$Re = \frac{L \overline{U}}{\gamma} \tag{4}$$

wherein:
L=Pipe Diameter (m);
U=Average pipe velocity (m/s);
μ=Coefficient of Viscosity, or Absolute Viscosity (kg/ms) or (Ns/m²);
γ=Kinematic Viscosity (m²/s).

According to an embodiment of the present invention, the calculated density and viscosity measurements may be provided directly to a flow computer and/or flow meter and the operation of the flow meter can be adjusted. Thus, the system of the present invention, in which a flow meter is previously-calibrated at least once against Reynolds number, can provide accurate flow measurements when the fluid in the pipeline changes.

| Terms: | | |
|---|---|---|
| ṁ | Mass Flow Rate | Kg/s |
| Cd | Flow Conditioner Coefficient of Discharge | $C_d = \dfrac{\text{Mass flow Actual}}{\text{Mass flow theoretical}}$ |
| $E_v$ | Velocity of approach factor | $\dfrac{1}{\sqrt{1-\beta^4}}$ |
| β | $d/D = \sqrt{\dfrac{\text{total area of holes or open areas}}{\text{area of pipe}}}$ | |
| d | Flow conditioner equivalent d | M (meters) |
| ΔP | Flow Conditioner Differential pressure | Pa |

-continued

| | Terms: | |
|---|---|---|
| ṁ | Mass Flow Rate | Kg/s |
| ρ | Density | Kg/m³ |
| k | Pressure loss coefficient for flow conditioner at Re | Dimensionless |
| γ | Viscosity | |
| φ | CPA fluid dynamic coefficient | Dimensionless |

In a specific embodiment, the flow conditioner may comprise a plate having through holes arranged in one or more concentric rings. The flow conditioner may be an integral, unitary body machined out of the same material. Thus, the flow conditioner does not include any tube bundles or combination of welded tubes. In a specific embodiment, suitable flow conditioners include, but are not limited to, CPA TBR®, CPA 50E®, CPA 55E®, CPA 65E® flow conditioners, available from Canada Pipeline Accessories, Inc. of Calgary, Canada. Flow conditioners are not mixers, but rather correct the flow profile of the fluid such that the fluid forms a fully developed flow profile.

The mixer may be any mixing device, such as a static mixer and/or pre-mixer. In specific embodiments, the mixer may be at least one static mixer, pre-mixer, or any combination thereof available from Canada Pipeline Accessories, Inc. of Calgary, Canada.

As used herein "substantially", "generally", "about", and other words of degree are relative modifiers intended to indicate permissible variation from the characteristic so modified (e.g., ±0.1%, ±0.5%, ±1.0%, ±2%, ±5%, ±10%, ±20%). It is not intended to be limited to the absolute value or characteristic which it modifies but rather possessing more of the physical or functional characteristic than its opposite, and preferably, approaching or approximating such a physical or functional characteristic.

Although the present invention has been described in terms of particular exemplary and alternative embodiments, it is not limited to those embodiments. Alternative embodiments, examples, and modifications which would still be encompassed by the invention may be made by those skilled in the art, particularly in light of the foregoing teachings.

Those skilled in the art will appreciate that various adaptations and modifications of the exemplary and alternative embodiments described above can be configured without departing from the scope and spirit of the invention. Therefore, it is to be understood that, within the scope of the appended claims, the invention may be practiced other than as specifically described herein.

What is claimed is:

1. A system for operating a flow meter in a pipeline, comprising:
at least one flow conditioner or mixer installed in a pipeline;
at least one flow meter installed downstream from the at least one flow conditioner or mixer for measuring velocity of a fluid in the pipeline;
a pair pressure transmitters for measuring fluid pressure at a first side and a second side of the at least one flow conditioner or mixer; and
a flow computer, connected to the pair of pressure transmitters and to the at least one flow meter, and comprising 1) at least one database having experimental Reynolds number data for the at least one flow meter for a plurality of fluids, and 2) a processor having programmable logic for calculating viscosity of a fluid in the pipeline and operating the flow meter when the fluid in the pipeline changes.

2. The system according to claim 1, wherein the flow meter is an ultrasonic meter.

3. The system according to claim 1, wherein the flow meter is a turbine meter.

4. The system according to claim 1, the flow conditioner comprising a plate having a plurality of through holes arranged in one or more concentric rings.

5. The system according to claim 1, wherein the system does not comprise a flow meter proving device.

6. The system according to claim 1, wherein the system does not comprise a viscometer.

7. The system according to claim 1, wherein the pipeline is an oil, crude oil, or liquified natural gas pipeline.

8. A method for operating a flow meter in a pipeline, comprising:
measuring a pressure of the fluid on a first and a second side of at least one flow conditioner or mixer;
measuring velocity of a fluid in a pipeline with a flow meter downstream of the at least one flow conditioner or mixer;
with an initial estimate of the fluid density, calculating a k factor from the Euler equation;
obtaining a first Reynolds number from the calculated k factor and from first experimental Reynolds number data for the flow meter for a plurality of fluids;
calculating a coefficient of discharge Cd for the fluid; and
obtaining a second Reynolds number from the calculated Cd and from second experimental Reynolds number data for the flow meter for a plurality of fluids.

9. The method according to claim 8, further comprising reiterating the method until the first Reynolds number and the second Reynolds number are a substantially similar third Reynolds number.

10. The method according to claim 9, further comprising calculating the viscosity of the fluid from the substantially similar third Reynolds number.

11. The method according to claim 10, further comprising providing density and viscosity measurements directly to the flow meter when a fluid in the pipeline changes.

12. The method according to claim 8, wherein the flow meter is calibrated once against Reynolds number for a plurality of fluids.

13. The method according to claim 8, wherein the fluid is oil, crude oil, or liquified natural gas.

14. The method according to claim 8, wherein:
the first experimental data comprises k factor versus Reynolds number; and
the second experimental data comprises Cd versus Reynolds number data.

* * * * *